(12) United States Patent
Kimmig et al.

(10) Patent No.: US 12,403,320 B2
(45) Date of Patent: Sep. 2, 2025

(54) HEAD PART OF AN IMPLANTABLE DEVICE, METHOD FOR PRODUCING THE HEAD PART AS WELL AS A PLUG ASSEMBLY WHICH CAN BE FITTED INTO THE HEAD PART

(71) Applicant: Neuroloop GmbH, Freiburg (DE)

(72) Inventors: Fabian Kimmig, Freiburg (DE); Tim Boretius, Freiburg (DE)

(73) Assignee: Neuroloop GmbH, Freiburg (DE)

( * ) Notice: Subject to any disclaimer, the term of this patent is extended or adjusted under 35 U.S.C. 154(b) by 519 days.

(21) Appl. No.: 17/922,138

(22) PCT Filed: May 4, 2021

(86) PCT No.: PCT/EP2021/061682
§ 371 (c)(1),
(2) Date: Oct. 28, 2022

(87) PCT Pub. No.: WO2021/224231
PCT Pub. Date: Nov. 11, 2021

(65) Prior Publication Data
US 2023/0211166 A1    Jul. 6, 2023

(30) Foreign Application Priority Data

May 5, 2020    (DE) .................... 10 2020 112 084.2

(51) Int. Cl.
*A61N 1/375*    (2006.01)
(52) U.S. Cl.
CPC ......... *A61N 1/3754* (2013.01); *A61N 1/3758* (2013.01)
(58) Field of Classification Search
CPC ..... A61M 5/14276; A61N 1/05; A61N 1/375; A61N 1/3752; A61N 1/3754;
(Continued)

(56) References Cited

U.S. PATENT DOCUMENTS 6,390,843 B1    5/2002   Lim
8,267,708 B1    9/2012   Sochor
(Continued)

FOREIGN PATENT DOCUMENTS

DE    102012010901    12/2012
DE    202013012073    3/2015
(Continued)

OTHER PUBLICATIONS

Communication, International Search Report and Written Opinion for PCT/EP2021/061682, mailed Aug. 10, 2021, 12 pages.
(Continued)

*Primary Examiner* — George Manuel
(74) *Attorney, Agent, or Firm* — Fitch, Even, Tabin & Flannery LLP

(57) ABSTRACT

The invention is a head part of an implantable device, method of production thereof and a plug which can be fitted into the head part. The head part comprises a housing which has at least one blind hole plug contact socket with a socket opening as well as a socket base axially opposite the socket opening, along which at least one electrically conductive contact ring element and an electrically insulating, elastically deformable sealing ring, which are enclosed by a solidified casting compound, are joined together coaxially axially. Arranged within the head part is at least one second blind hole plug contact socket with a socket opening as a socket base axially opposite the socket opening, along which at least one electrically conductive contact ring element and an electrically insulating, elastically deformable sealing ring is located, which are enclosed by the solidified casting compound, are joined together in a coaxial arrangement and in an axially serial sequence.

17 Claims, 2 Drawing Sheets

(58) Field of Classification Search
CPC .. A61N 1/3758; H01R 13/521; H01R 13/639; H01R 2201/12; H01R 24/58
See application file for complete search history.

(56) References Cited

U.S. PATENT DOCUMENTS

| | | | |
|---|---|---|---|
| 10,471,251 B1 | 11/2019 | Manicka | |
| 2003/0018364 A1 | 1/2003 | Belden | |
| 2005/0043765 A1 | 2/2005 | Williams | |
| 2008/0077190 A1 | 3/2008 | Kane | |
| 2011/0004279 A1 | 1/2011 | North | |
| 2012/0259381 A1* | 10/2012 | Smith | A61N 1/36125 607/46 |
| 2013/0245710 A1 | 9/2013 | Foster | |
| 2014/0237806 A1 | 8/2014 | Smith | |
| 2015/0142092 A1 | 5/2015 | Vadlamudi | |
| 2016/0100887 A1 | 4/2016 | Wu | |
| 2020/0077953 A1 | 3/2020 | Manicka | |

FOREIGN PATENT DOCUMENTS

| | | |
|---|---|---|
| DE | 102017222364 | 6/2019 |
| DE | 102018124307 | 4/2020 |
| EP | 2134418 | 12/2009 |
| WO | 2018222973 | 12/2018 |
| WO | 2019115176 | 6/2019 |

OTHER PUBLICATIONS

International Search report for PCT/EP2018/081922 ; mailed Jan. 31, 2019; 22 pages.
DE102012010901 machine translation, 2022.
DE102017222364 machine translation, 2022.
DE202013012073 machine translation, 2022.
WO2019115176 machine translation, 2022.

* cited by examiner

HEAD PART OF AN IMPLANTABLE DEVICE, METHOD FOR PRODUCING THE HEAD PART AS WELL AS A PLUG ASSEMBLY WHICH CAN BE FITTED INTO THE HEAD PART

CROSS-REFERENCE TO RELATED APPLICATIONS

Reference is made to International Application No. PCT/EP2021/061682, filed May 4, 2021, which claims priority to German Patent Application No. 10 2020 112 084.2, filed May 5, 2020, the contents of which are incorporated herein by reference in their entirety.

BACKGROUND OF THE INVENTION

Field of the Invention

The invention relates to a head part of an implantable device, its method of production and a plug assembly which can be fitted into the head part. The head part comprises a head part housing which has at least one blind hole-type plug contact socket with a socket opening as well as a socket base lying axially opposite the socket opening, along which at least one electrically conductive contact ring element and an electrically insulating, elastically deformable sealing ring, which are enclosed by a solidified casting compound, are joined together in a coaxial arrangement and in an axially serial sequence.

Description of the Prior Art

Implantable medical devices for the purpose of electrical stimulation of local intracorporeal tissue or nerve regions, in short implantable pulse generators (IPG), for example for cardiac treatment, defibrillation, pacemakers as well as resynchronization applications, for neurostimulation measures, such as spinal cord simulation, brain stimulation or vagus nerve stimulation to name but a few, as a general rule comprise a self-contained housing which contains components for electrical pulse generation. At least one electrical energy source and an electrical circuit structure are connected thereto. In addition, adjoining the housing is a so-called head part, which contains an electrical contact arrangement connected to the energy supply and the electrical circuit structure, into which a socket assembly, which closes the head part in a fluid-tight manner, can be inserted, and is contacted with electrical supply and outlet leads for the intracorporeal local application of electrical stimulation signals, as well as, if necessary, the supply of intracorporeally locally picked up electrical signals to the electrical circuit structure present in the housing.

Described in document EP 2 134 418 B1 is a head part of an implantable medical device of the type in question which along a joint seam comprises two head part housing halves that can be joined together and into which in serial sequence semi-cylindrical recesses are introduced that are separated by intermediate walls and into which electrically conductive contact ring elements and electrically insulating sealing rings are inserted each in serially alternating order. The head part therefore comprises an arrangement of electrically insulated contact ring elements that are coaxially orientated with regard to each other, for the electrical connection of a lateral access is provided in the head part through which an electrical plug assembly can be inserted in a fluid-tight manner into a hollow space enclosed by all the annular contact ring elements.

Document DE 10 2012 010 901 A1 discloses a method for positioning and holding electrical contacts and seals within a head part for electrical contact to a medically implantable device. Into one side of the head part housing, which is made of a biocompatible and electrically insulating material, a blind hole bore is made, into which electrically conductive and annular sealing elements are inserted in an alternating sequence and which enclose a hollow space into which a pin-like plug assembly can be introduced. Within the head part, each of the annular contact rings is connected by way of an electrical connection line to electrical components located within the housing of the medical implantable device.

Disclosed in document DE 20 2013 012 073 U1 is a plug boring module assembly, for the assembly of which a number of contact rings and sealing elements are arranged in alternating order along a pin-like assembly tool. By means of a clamping device, all contact rings and sealing elements arranged along the assembly tool are clamped to each other through the application of an axial joining force. Used for conserving the joining force is a sleeve element mounted by a grub screw in an axially fixed manner on the assembly tool, which together with the assembly tool head at the end, axially delimits the arrangement of contact rings and sealing elements on both sides. In this clamped state, the arrangement is cast in a hardenable casting compound, which in the solidified state takes up the joining force.

In place of a grub screw as the fixing aid at the end for conserving the axial joining force acting on the sequence of contact rings and sealing ring elements arranged along the pin-like assembly tool, in document WO 2019/115176 A1 it is proposed to use an assembly plate provided with an opening and internal thread, into the internal thread opening at which the pin-like assembly tool with an external thread arranged on its end is inserted.

Inferred from document US published patent application 2008/0077190 A1 is a head part that comprises two plug contact sockets, extending in parallel and laterally offset with regard to each other, for the insertion of a coaxial plug part. Coaxially to the sockets, opening out at the end on the socket base, is a face side end of a glass fiber assembly, which at its other fiber end is connected to an optical light pulse generator.

Document US published patent application 2011/0004279 A1 describes a head part, via which two electrical plug parts can be electrically connected to each other through coaxial insertion into a common socket channel by way of two axially opposite socket channel openings.

SUMMARY OF THE INVENTION

The invention modifies a head part of an implantable medical device. Its method of production as well as a plug assembly can be fitted into the head part in such a way that in addition to the previously known generation, transmission and application of electrical stimulation signals, it is possible to increase the functional scope of implantable pulse generators (IPG) without significantly changing their size.

The head part of an implantable medical device according to the invention, with a head part housing which has at least one first blind hole plug contact socket with a socket opening as well as a socket base lying axially opposite the socket opening, along which at least one electrically conductive contact ring element and an electrically insulating, elastically deformable sealing ring, which are enclosed by a solidified casting compound, are joined together in a coaxial arrangement and in an axially serial sequence. Arranged within the head part housing is at least one second blind hole-type plug contact socket with a socket opening as well as a socket base lying axially opposite the socket opening along which at least one electrically conductive contact ring element as well as an elastically deformable sealing ring, which are enclosed by a solidified casting compound, are joined together in a coaxial arrangement and in an axially serial sequence. The socket bases of the at least two plug contact sockets are each delimited by a connection means at least partially enclosed by the solidified casting compound, with the connection including a through channel, which on both sides opens out into the blind hole-type plug contact sockets.

The invention makes use of the opening in the assembly plate provided with an internal thread which is described in aforementioned document WO 2019/115176 A1 and which there, after removal of the assembly tools from the completed head part, otherwise has no function, in order to direct a media flow of any kind through the opening. The assembly plate, which in the aforementioned prior art can be considered as a type of lost component which is completely enclosed by the casting compound of the head part and within the solidified casting compound otherwise has no function for the further operation of the head part as well as the implantable pulse generator (IPG) connected to the head part, forms the central component of the modified head part according to the invention, which acquires the additional function of a connection channel through which a media flow can be directed from one blind hole-type plug contact socket to the other blind hole-type plug contact socket. This provides innovative applications for the implant, which is known per se having the main function which is the intracorporeal electrical stimulation of at least one local tissue and nerve regions, remains unaffected.

In the manner according to the invention, the connection, which directly or indirectly delimits the socket bases of the at least two plug contact sockets, also acts as a media coupling piece, via or through which a medium of predetermined choice can be transferred from one plug contact socket into the area of the other plug contact socket. Insertable in a detachably fixed manner into each of the two plug contact sockets is a plug assembly modified in accordance with the invention, which is appropriately designed and adapted for insertion into one of the blind hole plug contact sockets of the head described above. More particularly, the plug assemblies comprise a plug body with at least one interior hollow channel which at one side opens onto distal plug body end. In addition, the distal plug body ends have a joint contour which when the plug assembly is fitted within the plug contact socket ensures a flush transition of the hollow channel on the plug side to the through channel within the connection and opening into the blind hole-type plug contact socket. Through this, as loss-free as possible, the connection and further conveying or transmission of a medium being transmitted within the hollow channels or the through channel between the two plug assemblies via the connection is achieved.

Apart from that, the implantable plug assemblies are designed in manner known per se for the transmission of electrical signals and in the longitudinal extension of the plug comprises a serial sequence of plug contact rings as well as sealing rings or electrical insulation rings corresponding to the number and arrangement of the electrical contact ring elements and sealing rings along the plug contact sockets.

In the joined state of the implantable plug assemblies within the plug contact sockets provided on the head part side, the electrical functionality of the implantable device for the application of electrical stimulation signals is unrestrictedly retained in spite of a modified head part and modified plug assemblies. Via the hollow channels additionally provided and designed as media channels on the plug side and connectable by way of the through channel within the connection, at least one of intracorporeal media transportation and intracorporeal media application occur a function of a respectively selected medium, that is a in gas or fluid transportation or application or a light application.

A first embodiment has the configuration of the hollow channels as the through channel as a fluid line in each case, along which a gaseous or fluid medium can be conveyed or transported.

Directly adjoining each of the plug assemblies projecting from the head part, is a preferably flexibly designed output line, extending along which is at least one electrical line, via which the electrical stimulation signals and/or endogenous, sensor-recorded electrical signals can be transmitted, as well as the at least one hollow channel for media transmission.

Depending on the intracorporeal arrangement and placement of the output lines from the plug assemblies, various intracorporeal regions can be fluidically connected to each other via the hollow channels connected to both plug assemblies and the through channel connecting the two hollow channels to each other.

In a simplest variant, the fluidic connection can occur purely passively, without a fluidic conveying device.

Along the through channel within the connection channel, a preferred form of embodiment has a fluid pump that is controlled by connection to electrical components which are arranged within the implantable device for electrical pulse generation. The fluid pump that can be operated in a controlled manner making possible an intracorporeal fluid flow which transfers fluid from one region of the body, into which the hollow channel connected to one of the two plug assemblies opens, to another region of the body into which the hollow channel connected to the other plug assembly opens. Activation of the fluid pump and determination of the flow direction and flow rate are defined by way the electrical components contained in the implantable device.

In a further embodiment, the implantable device comprises a fluid reservoir which is connectable via a connection line to the through channel within the connection, so that preferably via a valve which is controllable along the connection line, an additional fluid, preferably of a gaseous or fluid active substance, can be mixed into the fluid flow passing through the through channel.

Alternatively, or in combination, to create the hollow channels as well as the though channel as a fluid line, a further embodiment includes a light-guiding medium along the hollow channels as well as the through channel. In this way, two intracorporeal region which are arranged spatially separated from each other, can be optically connected to one another. For this, along each of the hollow channels connected to the plug assemblies, at least one light guide is fitted with guide opening onto the plug body ends of the plug assembly. When in the inserted state within the head part, the light guide ends are coupled in an as loss-free manner as possible to a light guide within the through channel. Preferably along the through channel within the connection is also an optical device which can have an influence on the light transmitted along the individual light guides. For example, along the through channel at least one of an optical coupling and a output element is provided, by which the light of a light source provided within the implantable device can be coupled along at least one of the light guide and the device by which the light for transmission of a light detector provided within the implantable device can be coupled out of the light guide.

Alternatively, or in addition to at least one of the optical coupling and the output element, an optical amplifier, and optical filter or switch can be positioned along the through channel of the connection, which are connected to corresponding electrical control components arranged within the implantable device.

Also suitable, as an alternative to or in combination with the aforementioned components for media transmission along the hollow channels as well as the through channel, an electrically conductive medium is provided at least one electrical connection lead, along which, in addition to the electrical leads that are connected anyway to the electrical contact ring elements for the purpose of tissue/nerve stimulation, the additional transmission of electrical signals between two spatially separated regions of the body becomes possible. Advantageously, in this case it is advisable to arrange an electrical component, such as, for example, an adjustable electrical resistor, an electrical amplifier or equivalent electrical components in the connection along the through channel in order to influence the current flow along the hollow channels.

In a further preferred form of embodiment, arranged within the head part, in particular on the connection or within the connection, is at least one sensor which can detect or record in a sensor-based manner, the medium being conveyed within the through channel at least quantitatively in terms of the conveyed volume, conveyed rate or light intensity. Depending on the type and design of the at least one sensor, it should be suitably arranged within the head part, for example, it is useful to at least one of electrically and mechanically connecting the at least one sensor directly or indirectly to one of the electrically conductive contact ring elements applied within the head part. Sensors from the following group can be considered as possible sensors: ultrasonic sensors, optical sensors, pressure sensors, Hall effect sensors, flow sensors, needle sensors, fluorescence sensors, and pressure sensors etc.

The at least one sensor is preferably connected to an electrical energy source which supplies electrical energy to the pulse generator within the medical device. Furthermore, the at least one sensor is connected to an evaluation and control, which is connected to an additional memory and a component within the connection along the through channel for influencing the media flow passing through the through channel. In this way it is possible to record a sensor-detected actual state of the medium flowing or conveyed along the through channel and to control or regulate the at least one component arranged along the through channel for influencing the medium flow as a function of a target-actual comparison.

The head part assembled according to the invention as well as the functionally modified plug assemblies for the transmission of a medium fluid, luminous flux or an electrical current, permits the shape and size of known medical implants of the type in question largely to be unchanged, but significantly expands their functionality and the therapeutic mode of action of comparable implants associated therewith. In this way, besides the electrical stimulation of at least one of intracorporeal local tissue and nerve regions, it is possible to additionally apply a fluid, light or electrical voltage.

The combined use of the connection originally acting as an assembly plate as a supporting structure and as a type of connection flange, allows an innovative method of production of such a head part. Thus, in a first processing step, the connection serves as a supporting plate in the conventional sense, i.e. the connection is arranged, together with the at least one contact ring element as well as the at least one sealing ring, along a first rod-shaped assembly tool, and serves as a mechanical counter-bearing to produce an axial clamping force. For this, the connection envisages a first opening with an internal thread, into which an outer thread applied at the end of the assembly tool can be fitted. By twisting the assembly tool relative to the connection, the contract ring elements positioned along the assembly tool as well as the sealing rings are tensioned with regard to each other. In the same way, the connection serves as a supporting structure and a mechanical counter-bearing for producing a clamping force along the contact ring elements and sealing rings arranged on a second assembly tool. For this, the connection has a second opening with an internal thread which is connected to the first opening by way of the through channel.

In a next step, the connection with the two assembly tools attached thereto and the axial succession, mounted thereon, of the at least one contact ring element and the at least one sealing ring element, is encased with a solidifiable casting compound, that is present in fluid form, in order to create the head part. After solidification of the casting compound, the rod-shaped assembly tools are released from the connection means and removed. By removing the assembly tools, the through channel passing through the connection means opens on both sides into the blind hole-type plug contact sockets of the head part formed by removing the assembly tools.

BRIEF DESCRIPTION OF THE DRAWINGS

The invention will be described below without restricting the general inventive concept by way of examples of embodiment with reference to the drawings. In these.

DETAILED DESCRIPTION OF THE INVENTION

Figure 1:
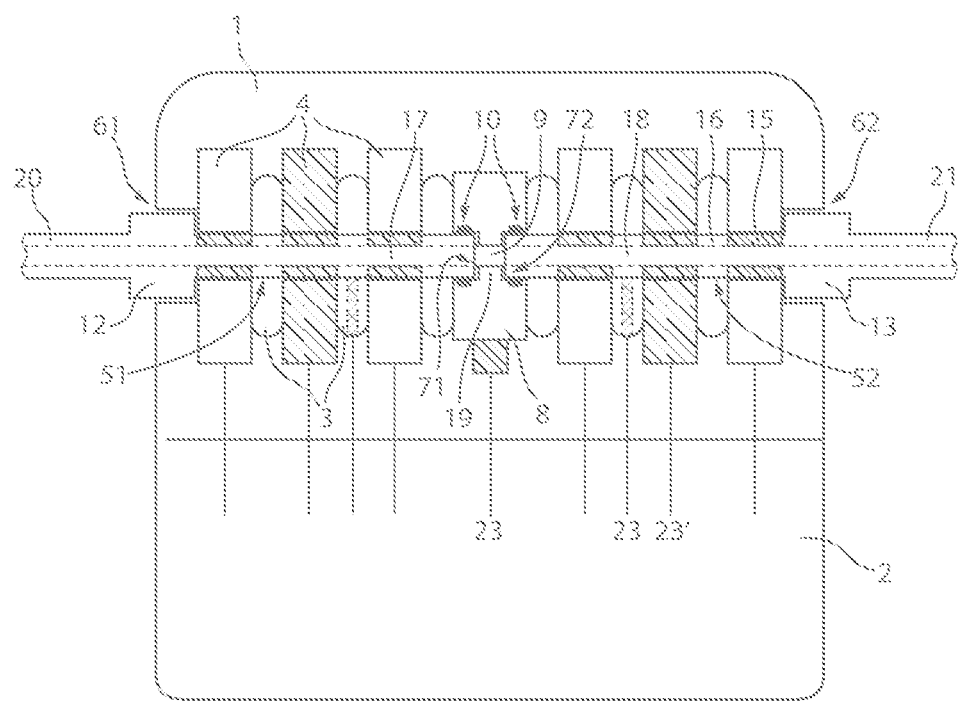
FIG. 1 Shows a head part with an implantable device for electrical pulse generation as a connector variant.

FIG. 1 shows a schematic view of a head part 1 that is combined with an implantable, medical device 2 designed as a pulse generator to form a component. Arranged in an axially serial sequence in the head part 1 made of a solidifiable casting compound are electrically insulating, electrically deformable sealing rings 3 as well as electrically conducting contact rings 4, each in alternating order. The sealing rings 3 as well as the electrical contact rings 4 encompass a blind hole-type plug contact socket 51, 52 which has a socket opening 61, 62 that is accessible on the outer wall of the head part 1. The socket bases 72, 73 which are opposite the socket openings 71, 72 are delimited by a common connection 8 that, for the production of the head part 1 and in particular for axially lining up the sealing rings 3 and electrical contact elements 4, functions as a mechanical counter-bearing for two assembly tools each used for assembly purposes. For this, the connection means 8 has a through channel 9 that completely passes through the connection 8, along which, at least in parts on the through channel openings, an internal thread 10 is incorporated.

Fitted into each of the blind hole-type plug contact sockets 51, 52 is a plug assembly 12, 13 finished in accordance with the invention which each comprise a plug body, adapted to the dimensions and shape of the plug contact sockets 51, 52, on the outer perimeter of which corresponding counter contact elements 15 are arranged corresponding to the arrangement of the electrical contact ring elements 4. Between the counter contact elements 15, electrically insulating plug body areas are provided. With regard to the electrical contacting of the plug contact assemblies 12, 13 within each of the blind hole-like plug contact sockets 51, 52 of the head part, the device illustrated in FIG. 1 does not differ from comparable plug assemblies of the type in question.

According to the invention, the plug contact assemblies 12, 13 has a media channel formed as a hollow channel 17, 18 that centrally projects through the plug body which in the area of the socket base 71, 72 flushly adjoins the media channel 9 opening into the blind hole plug contact sockets 51, 52 formed as a butt joint. Depending on the type and design of the hollow channel 17, 18 as well as the through channel 9, the connection between the through channel 9 and the respective hollow channel 17, 18 on the plug side, should be a low-loss or loss-free connection and provides transmission of the medium passing through the hollow channels. For this, at least one of an additional sealing and joint contour 19 is optionally introduced within the connection means 8 for a seamless transition between the hollow channels 17, 18 and the through channel 9.

The plug contact assemblies 12, 13 are each connected to an output line 20, 21, which in addition to the at least one electrical line, for electrical stimulation signal transmission, which is not shown, includes the hollow channel 17, 18.

The head part 1 shown in FIG. 1 in the first instance acts as a connector or connection part between two plug assemblies 12, 13, the hollow channels 17, 18 which connect to each other via the through channel 19 in a manner that is flush and loss-free for possible media transmission.

The example of embodiment shown in FIG. 1 shows two parallel and coaxially orientated plug contact sockets 51, 52, the openings 61, 62 of which open out on diametrically opposite housing sides of the head part 1. Equally, it is possible to provide two plug contact sockets orientated in parallel next to each other within the head part with the openings opening out at the same side of the head part 1. In this case, the through channel 9 passing within the connection means is semi-arched in order to connect the media channels on the plug side, that open out on the respective socket bases, to each other to be flush.

It is also possible to provide three or more plug contact sockets in the head part, which are each connected to each other with a through channel that branches off three of more times.

For the detection of the media passing through the hollow channels 17, 18, for example in the form of a gaseous or liquid fluid, light or electrical current, a preferred variant embodiment envisages the providing of at least one sensor 23 with the head part 1. Depending on the type and design of the sensor 23, it is arranged directly on, or integrated into the connection 8, and on at least one of the sealing rings 3 or on at least one of the electrical contact ring elements 4. The type and application of the at least one sensor 23 is guided by the medium being transmitted along the hollow channels 17, 18. The sensor 23 can be suitably selected from the following sensor types: Hall effect sensors, optical sensors, flow sensors, ultrasonic sensors, temperature sensors, pressure sensors etc.

Figure 2:
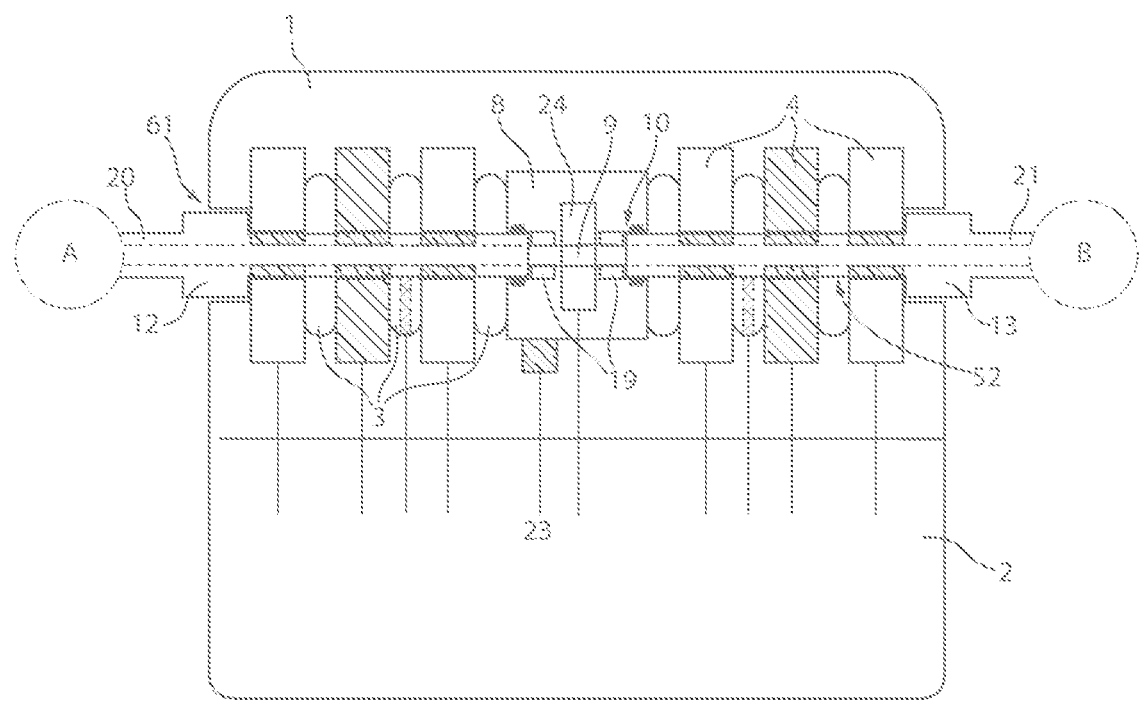
FIG. 2 Shows a head part with an implantable device for generating electrical stimulation signals with a component within the connection means that influences the media flow.

In FIG. 2, in contrast to the head part 1 illustrated in FIG. 1, within the connection means 8 an additional component 24 is arranged along the through channel 9 which has an influence on the medium passing through the hollow channels 17, 18 as well as the through channel 9. In FIG. 2, structurally and functionally equivalent components which have already been described in connection with the example of embodiment shown in FIG. 1, are provided with the same reference numbers.

In the case of hollow channels 17, 18 which are fluid lines, the component arranged along the through channel 9 is preferably a fluid pump. Using the fluid pump, it is possible to convey, for example, intracorporeal fluid from one region of the body A to another region of the body B. Additionally, the component 24 can contain a filter for cleaning the fluid passing through the through channel 9.

It is also possible to provide the hollow channels 17, 18 as well as the through channel 9 with a light guide. In this case, the component 24 can be an optical unit, for example, an optical amplifier, an optical filter or switch or at least one of an optical coupling and output element. Possible in this context is the optical stimulation of the intracorporeal regions A, B with light, in addition to the electrical stimulation that can also be brought about by the implant. For this, within the implantable device 2, it is matter of providing at least one light source which is optically coupled to the unit 24. Equally, a photodetector can be contained within the implantable device 2 which is capable of detecting intracorporeal optical signals transmittable via the optical light guide.

Finally, in the case of an electrical lead along the hollow channels 17, 18 as well as the through channel, the component 24 can be designed in the form of an adjustable electrical resistor or an electrical amplifier.

LIST OF REFERENCE NUMBERS

1 Head part
2 Implantable device, IPG
3 Sealing ring
4 Contact ring element
51, 52 Plug contact socket
61, 62 Opening
71, 72 Socket base
8 Connection
9 Through channel
10 Inner thread
12, 13 Plug
14 N.N.
15 Counter contact element
16 Plug body area
17, 18 Hollow channel
19 At least one of a sealing and joint contour
20, 21 Output line
23 Sensor
24 Fluid, optical or electrical component

The invention claimed is:

1. A head part of an implantable medical device, comprising:
 a housing which has at least one first blind hole plug contact socket including a socket opening and a socket base axially opposite the socket opening, along which extends at least one electrically conductive contact ring and an electrically insulating, elastically deformable sealing ring which are enclosed by a solidified casting compound and are joined together coaxially in a sequence;

at least one second blind hole plug contact socket within the head part including a socket opening and a socket base axially opposite the socket opening between which at least one electrically conductive contact ring element and an electrically insulating elastically deformable sealing ring are located which are enclosed by the solidified casting compound to be joined together coaxially in a serial sequence;

the socket bases of the at least two plug contact sockets each being delimited by a connection at least partially enclosed by the solidified casting compound; and the connection includes a through channel which on both sides of the channel opens out into the blind hole plug contact sockets.

2. A head part according to claim 1, wherein:
the through channel is hollow.

3. A head part according to claim 2, wherein:
a fluid pump is located along the through channel.

4. A head part according to claim 1, wherein:
the through channel is partly filled with a light-guiding medium.

5. A head part according to claim 4, wherein:
an optical device chosen from one of an optical amplifier, an optical filter, a switch, and at least one optical input and output is located along the channel.

6. A head part according to claim 1, wherein:
the through channel is filled with an electrically conductive medium.

7. A head part according to claim 6,
the through channel contains one of an electrical component chosen from an adjustable electrical resistor or an electrical amplifier.

8. A head part according to claim 1, wherein:
the connection which is at least partially enclosed by the solidified casting compound is located on at least one sensor for detecting a medium contained within or an electrical current flow in the through channel.

9. A head part according to claim 8, wherein:
the at least one sensor is selected from a group of sensors of ultrasonic sensors, optical sensors, pressure sensors, Hall effect sensors, and a flow sensor.

10. A head part according to claim 8, wherein:
the at least one sensor is connected to an evaluation and a control.

11. A head part according to claim 1, wherein:
at least one sensor is at least one of electrically and mechanically connected to the at least one electrically conducting contact ring element.

12. A head part according to claim 1, wherein:
on sides facing the socket bases, the connection comprises a joint contour enclosing the through channel which has a media channel located within the plug contact socket coupled to the through channel without losses.

13. A head part according to claim 1, wherein:
the housing is mechanically and electrically connected to an implantable pulse generator.

14. A head part according to claim 1, wherein:
longitudinal axes of the first and the second blind hole plug contact sockets are orientated in parallel to each other with socket openings thereof opening on opposite sides or on a same side of the housing.

15. An implantable plug for insertion into the blind hole contact sockets according to claim 1, wherein:
the plug assembly comprises a body has at least one interior hollow channel which at one end opens out at a distal end of the plug; and the plug body end has a joint contour which when the plug assembly is fitted within the plug contact socket provides a flush joint of the hollow channel to the through channel within the connection element.

16. A plug assembly according to claim 15, wherein:
the hollow channel has a media channel through the channel contained in the connection.

17. A method for producing a head part according to claim 1, comprising:
the connection, the at least one contact ring element and the at least one sealing ring are located along the first blind hole plug contact socket on a first rod-shaped assembly tool, and are joined to each other in contact along the first rod-shaped assembly tool by an axial joining force;

the connection, the at least one contact ring element and the at least one sealing ring are arranged along the second blind hole plug contact socket along a second rod-shaped assembly tool, and are joined to each other in contact along the second rod-shaped assembly tool by a joining force;

the connection, arranged and joined along the first and second rod-shaped assembly tool, as well as the at least one contact ring and the at least one sealing ring of the first and the second blind hole plug contact socket are at least partially enclosed by a solidifiable casting compound that is present in flowable form; and releasing and removing the first and second rod-shaped assembly tool from the connection and the at least one contact ring element so that the least one sealing ring of the first and the second blind hole plug contact sockets after solidification of the casting compound forms of matrix so that at least one part of the head part housing supports the axial joining force.

* * * * *